(12) United States Patent
Dyballa et al.

(10) Patent No.: US 9,737,884 B2
(45) Date of Patent: Aug. 22, 2017

(54) PROCESS FOR CATALYTIC PREPARATION OF ALDEHYDES FROM OLEFINS USING MONOPHOSPHITE MIXTURES

(71) Applicants: Katrin Marie Dyballa, Recklinghausen (DE); Robert Franke, Marl (DE); Dirk Fridag, Haltern am See (DE); Dieter Hess, Marl (DE); Bart Hamers, VG Horst (NL); Frank Geilen, Haltern am See (DE)

(72) Inventors: Katrin Marie Dyballa, Recklinghausen (DE); Robert Franke, Marl (DE); Dirk Fridag, Haltern am See (DE); Dieter Hess, Marl (DE); Bart Hamers, VG Horst (NL); Frank Geilen, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/716,437

(22) Filed: May 19, 2015

(65) Prior Publication Data

US 2015/0336093 A1    Nov. 26, 2015

(30) Foreign Application Priority Data

May 20, 2014 (DE) .................. 10 2014 209 535
Feb. 16, 2015 (DE) .................. 10 2015 202 722

(51) Int. Cl.
| | | |
|---|---|---|
| B01J 31/22 | (2006.01) | |
| C07C 45/50 | (2006.01) | |
| B01J 31/18 | (2006.01) | |
| C07F 9/145 | (2006.01) | |

(52) U.S. Cl.
CPC ......... *B01J 31/2295* (2013.01); *B01J 31/185* (2013.01); *C07C 45/50* (2013.01); *C07F 9/145* (2013.01); *B01J 2231/70* (2013.01); *B01J 2531/822* (2013.01)

(58) Field of Classification Search
CPC ...... B01J 31/2295; B01J 31/185; C07F 9/145; C07C 45/50
USPC ......................... 568/454; 556/13; 252/182.3
See application file for complete search history.

(56) References Cited

U.S. PATENT DOCUMENTS

| | | |
|---|---|---|
| 5,306,839 A | 4/1994 | Sato et al. |
| 5,672,766 A | 9/1997 | Mori et al. |
| 6,153,800 A | 11/2000 | Gelling et al. |
| 7,928,267 B1 | 4/2011 | Puckette et al. |
| 2003/0001136 A1 | 1/2003 | Stevenson et al. |
| 2011/0196079 A1 | 8/2011 | Jakupca et al. |

FOREIGN PATENT DOCUMENTS

| | | |
|---|---|---|
| CN | 101288852 A | 10/2008 |
| CN | 102826973 A | 12/2012 |
| DE | 697 07 145 T2 | 6/2002 |
| JP | 2005-247982 A | 9/2005 |
| WO | WO 02/070625 A1 | 9/2002 |
| WO | WO 2010/015128 | 12/2010 |
| WO | WO 2014/056732 A1 | 4/2014 |
| WO | WO 2014/056737 A1 | 4/2014 |

OTHER PUBLICATIONS

Hugo Tricas, et al., "Bulky monophosphate ligands for ethane hydroformylation", Journal of Catalysis, 298, 2013, pp. 198-205.
Robert Franke, et al., "Applied Hydroformylation", Chemical Reviews, American Chemical Society, 2012, 112, pp. 5675-5732.
European Search Report issued Jul. 31, 2015 in Patent Application No. 15166048.7 (with English translation of categories of cited documents).
Manfred T. Reetz, et al., "The Influence of Mixtures of Monodentate Achiral Ligands on the Regioselectivity of Transition-Metal-Catalyzed Hydroformylation" Angewandte Chemie International Edition, vol. 44, XP055202904, 2005, pp. 2962-2964.
Anonymous, "Doverphos® S-9228 & Doverphose® S-9411 High Performance Phosphite Stabilizers" Dover Chemical Corporation, XP002742356, Jun. 10, 2011, 8 Pages.
Singapore Examination Report dated Feb. 4, 2016 for Application No. 10201503944P.
Office Action dated Aug. 15, 2016 in Japanese Patent Application No. 2015-103111 (submitting English translation only).
Office Action dated Aug. 18, 2016 in Taiwanese Patent Application No. 104115793.
Gual, A. et al., "Design and Synthesis of Phosphite Ligands for Homogeneous Catalysis," *phosphorus(III) Ligands in Homogeneous catalysis: Design and Syntheeis, First Edition.* 2012.
Office Action dated Oct. 18, 2016 for Korean Application No. 10-2015-0069434 with English Translation.
Office Action dated Dec. 13, 2016 for Taiwanese Application No. 104115793 with English Translation.
German Search Report dated Feb. 4, 2015 for Application No. 10 2014 209 535.2.

*Primary Examiner* — Porfirio Nazario Gonzalez
(74) *Attorney, Agent, or Firm* — Oblon, McClelland, Maier & Neustadt, L.L.P.

(57) ABSTRACT

The catalytic preparation of an aldehyde from an olefin proceeds in the presence of a monophosphite mixture.

7 Claims, No Drawings

PROCESS FOR CATALYTIC PREPARATION OF ALDEHYDES FROM OLEFINS USING MONOPHOSPHITE MIXTURES

BACKGROUND OF THE INVENTION

Field of the Invention

The invention relates to processes for catalytic preparation of an aldehyde from an olefin using a monophosphite mixture, and to the novel monophosphite mixture itself.

Discussion of the Background

The reactions between olefin compounds, carbon monoxide and hydrogen in the presence of a catalyst to give the aldehydes comprising one additional carbon atom are known as hydroformylation or oxo synthesis. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Borner, "Applied Hydroformylation", Chem. Rev., 2012, DOI:10.1021/cr3001803.

The type of catalyst system and the optimal reaction conditions for the hydroformylation are dependent on the reactivity of the olefin used.

The different reactivity of isomeric octenes is likewise known (see B. L. Haymore, A. van Hasselt, R. Beck, Annals of the New York Acad. Sci., 415, 1983, p. 159-175). Via the different processes and catalysts, a multitude of olefins are available for the hydroformylation (see P. W. N. M. van Leeuwen, in Rhodium Catalyzed Hydroformylation, P. W. N. M. van Leeuwen, C. Claver (eds.), Kluwer, Dordrecht, 2000).

Technical olefin mixtures which are used as reactants for the oxo process often contain olefins of a wide variety of different structures, having different levels of branching, different double bond positions in the molecule and possibly also different carbon numbers. This is particularly true of olefin mixtures which have formed through di-, tri- or substantial oligomerization of olefins. Examples of technical olefin mixtures which are converted to the corresponding aldehyde mixtures by hydroformylation include tri- and tetrapropene, and di-, tri- and tetrabutene.

The abovementioned technical olefin mixtures often contain only small proportions of olefins having terminal double bonds. In order to prepare products in which more terminally hydroformylated aldehyde is present than in the original olefin mixture therefrom, it is necessary to hydroformylate under isomerizing conditions.

Suitable processes for this purpose are, for example, high-pressure hydroformylations with cobalt catalysts. However, disadvantages of these processes include the fact that a relatively large number of by-products such as alkanes, acetals and ethers are formed and that very severe reaction conditions (high temperature, high pressure) are necessary (see also Klaus-Diether Wiese, Dietmar Obst, Top. Organomet. Chem. 2006, 18, 1-33).

When rhodium complexes are used as catalyst, the ligand is another crucial factor for the product composition of the aldehydes. Unmodified rhodium-carbonyl complexes catalyze the hydroformylation of olefins having terminal and internal double bonds, where the olefins may also be branched, to give aldehydes having a high level of branching. The proportion of terminally hydroformylated olefin is much lower compared to the cobalt-catalyzed product.

The hydroformylation of olefins having internal double bonds over catalyst systems containing sterically demanding bisphosphite ligands proceeds with good selectivity in the case of long-chain olefins, but with an unsatisfactory activity (P. W. N. M. van Leeuwen, in Rhodium Catalyzed Hydroformylation, P. W. N. M. van Leeuwen, C. Clover (eds.), Kluwer, Dordrecht, 2000).

In Angew. Chem. Int. Ed. 2000, 39, No. 9, p. 1639-1641 by Bonier et al., phosphonites are used in hydroformylation, i.e. ligands having one P—C and two P—O bonds. The phosphonites described here, when used in hydroformylation, have n/iso selectivity (n/iso=the ratio of linear aldehyde (=n) to branched (=iso) aldehyde) of 0.61 to 1.57.

However, the preparation of these ligands based on a phosphonite structure, in the case of an industrial-scale synthesis, is much more complex than, for example, the preparation of phosphite ligands. This point is a crucial factor especially in the case of use of these ligands in an industrial scale process. The synthesis of the compounds used as ligands should be as inexpensive and simple as possible.

Rhodium-monophosphite complexes in catalytically active compositions, in contrast, are suitable for the hydroformylation of branched olefins having internal double bonds.

Since the 1970s, there have been descriptions of the use of "bulky phosphites" in hydroformylation (see, inter alia, van Leeuwen et al., Journal of Catalysis, 2013, 298, 198-205). These feature good activity, but the n/i selectivity for terminally hydroformylated compounds is in need of improvement.

As well as the use of pure ligands, the use of ligand mixtures has also been described in the literature.

US 20120253080 describes the use of monophosphites with bisphosphites. However, this combination has the disadvantage that the bisphosphites, although having good selectivity, have very low activity in the case of long-chain olefins and are therefore in need of improvement. In an industrial scale process, in addition to the selectivity for the desired product, the space-time yield or the activity of the catalyst system is an important factor with regard to the economic viability thereof. Moreover, the bisphosphites are frequently much more costly to prepare than, for example, the monophosphites.

EP 1 099 678 describes the use of phosphonites with bisphosphites. However, it is disadvantageous here that both ligand types are very costly to produce, and an industrial scale process can therefore hardly be economically viable. Moreover, the addition of the bisphosphite ligand noticeably affects the yield of the reaction, since these ligands are less active when dibutene, for example, is used as substrate.

WO 2007/149143 discloses mixtures of two to five triaryl phosphites which are liquid under ambient conditions. These triaryl phosphites have at least one alkyl substituent, more specifically a tert-butyl or tert-pentyl substituent. The mixtures are used as stabilizers/antioxidants for polymer resins, especially thermoplastic resins or elastomers.

U.S. Pat. No. 8,258,215 B2 describes phosphites which are used for stabilizing polymers. These phosphites have either one aromatic radical and two aliphatic radicals or two aromatic radical and one aliphatic radicals.

It is therefore desirable to develop a catalyst system which does not have the disadvantages exhibited in the related art.

SUMMARY OF THE INVENTION

It was therefore an object of the present invention to provide a catalyst system for hydroformylation of olefins, with which branched, unbranched, terminal and internal olefins can be terminally hydroformylated with high yields and selectivities, i.e. very substantially linear aldehydes can be prepared.

In addition, the cost/benefit ratio of the ligands being used is to be optimized.

This and other objects have been achieved by a mixture, comprising:

a compound of the structure Ia:

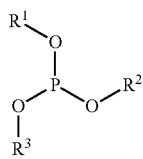

Ia wherein $R^1$ is selected from the group consisting of
—$(C_1-C_{12})$-alkyl, and —$(C_3-C_{12})$-cycloalkyl,
and
$R^2$, $R^3$ are each independently selected from the group consisting of
—$(C_1-C_{12})$-alkyl, —$(C_6-C_{20})$-aryl, and —$(C_3-C_{12})$-cycloalkyl,
the $R^2$ and $R^3$ radicals are optionally bridged to one another, and optionally have a —$(C_6-C_{20})$-aryl-$(C_6-C_{20})$-aryl unit,
wherein the alkyl, cycloalkyl and aryl groups mentioned are optionally substituted,
and
comprising a compound of the structure IIb:

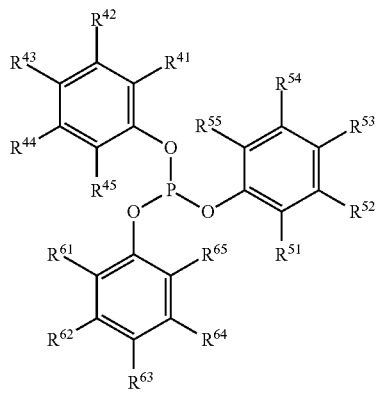

IIb wherein $R^{41}$, $R^{42}$, $R^{43}$, $R^{44}$, $R^{45}$, $R^{51}$, $R^{52}$, $R^{53}$, $R^{54}$, $R^{55}$, $R^{61}$, $R^{62}$, $R^{63}$, $R^{64}$, $R^{65}$ are each independently selected from the group consisting of
—H, —$(C_1-C_{12})$-alkyl, —O—$(C_1-C_{12})$-alkyl, —O—$(C_6-C_{20})$-aryl, —$(C_6-C_{20})$-aryl, -halogen, —COO—$(C_1-C_{12})$-alkyl, —CO—$(C_1-C_{12})$-alkyl, —CO—$(C_6-C_{20})$-aryl, —COOH, and —OH.

In another embodiment, the present invention relates to a complex mixture, comprising:
a mixture as described above, and
a metal atom selected from the group consisting of Rh, Ru, Co, and Ir.

In yet another embodiment, the present invention relates to a process for hydroformylation of an olefin, comprising:
a) initially charging an olefin,
b) adding a mixture comprising a compound of the structure IIIa:

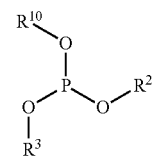

IIIa wherein $R^{10}$ is selected from the group consisting of
—$(C_1-C_{12})$-alkyl, —$(C_6-C_{20})$-aryl, and —$(C_3-C_{12})$-cycloalkyl, and
$R^2$, $R^3$ are each independently selected from the group consisting of
—$(C_1-C_{12})$-alkyl, —$(C_6-C_{20})$-aryl, and —$(C_3-C_{12})$-cycloalkyl,
the $R^2$ and $R^3$ radicals are optionally bridged to one another, and
optionally have a —$(C_6-C_{20})$-aryl-$(C_6-C_{20})$-aryl unit,
wherein the alkyl, cycloalkyl and aryl groups mentioned are optionally substituted,
and a compound of the structure IIa:

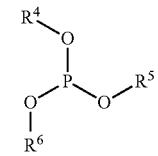

IIa wherein $R^4$, $R^5$, $R^6$ are each independently selected from the group consisting of
—$(C_1-C_{12})$-alkyl, —$(C_6-C_{20})$-aryl, and —$(C_3-C_{12})$-cycloalkyl, two $R^4$ and $R^5$ or $R^5$ and $R^6$ or $R^6$ and $R^4$ radicals are optionally bridged to
one another, and optionally have a —$(C_6-C_{20})$-aryl-$(C_6-C_{20})$-aryl unit,
wherein the alkyl, cycloalkyl and aryl groups mentioned are optionally substituted;
c) adding a compound comprising one of the following metals: Rh, Ru, Co, or Ir, to obtain a reaction mixture,
c) feeding $H_2$ and CO into the reaction mixture,
d) heating the reaction mixture, to convert the olefin to an aldehyde,
wherein the additions in process steps b) and c) can also be effected in one step through the addition of a corresponding complex mixture.

DETAILED DESCRIPTION OF THE INVENTION

The present invention relates to a mixture comprising a compound of the structure Ia:

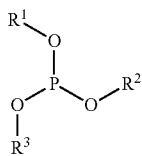

where
R¹ is selected from:
—(C₁-C₁₂)-alkyl, —(C₃-C₁₂)-cycloalkyl, and
R², R³ are each independently selected from:
—(C₁-C₁₂)-alkyl, —(C₆-C₂₀)-aryl, —(C₃-C₁₂)-cycloalkyl,
the R² and R³ radicals may also be bridged to one another, and may have a —(C₆-C₂₀)-aryl-(C₆-C₂₀)-aryl unit,
where the alkyl, cycloalkyl and aryl groups mentioned may be substituted,
and
comprising a compound of the structure IIb:

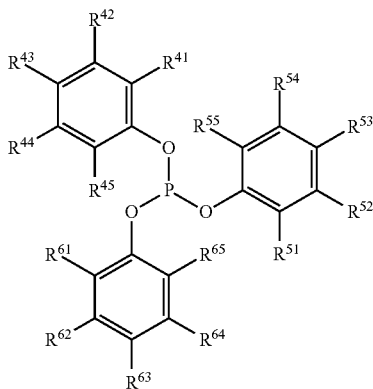

where
R⁴¹, R⁴², R⁴³, R⁴⁴, R⁴⁵, R⁵¹, R⁵², R⁵³, R⁵⁴, R⁵⁵, R⁶¹, R⁶², R⁶³, R⁶⁴, R⁶⁵ are each independently selected from:
—H, —(C₁-C₁₂)-alkyl, —O—(C₁-C₁₂)-alkyl, —O—(C₆-C₂₀)-aryl, —(C₆-C₂₀)-aryl, -halogen, —COO—(C₁-C₁₂)-alkyl, —CO—(C₁-C₁₂)-alkyl, —CO—(C₆-C₂₀)-aryl, —COOH, —OH.

(C₁-C₁₂)-Alkyl may in each case be unsubstituted or substituted by one or more identical or different radicals selected from (C₃-C₁₂)-cycloalkyl, (C₃-C₁₂)-heterocycloalkyl, (C₆-C₂₀)-aryl, fluorine, chlorine, cyano, formyl, acyl and alkoxycarbonyl.

(C₆-C₂₀)-Aryl may in each case be unsubstituted or substituted by one or more identical or different radicals selected from —H, —(C₁-C₁₂)-alkyl, —O—(C₁-C₁₂)-alkyl, —O—(C₆-C₂₀)-aryl, —(C₆-C₂₀)-aryl, -halogen (such as Cl, F, Br, I), —COO—(C₁-C₁₂)-alkyl, —CONH—(C₁-C₁₂)-alkyl, —(C₆-C₂₀)-aryl-CON[(C₁-C₁₂)-alkyl]₂, —CO—(C₁-C₁₂)-alkyl, —CO—(C₆-C₂₀)-aryl, —COOH, —OH, —SO₃H, —SO₃Na, —NO₂, —CN, —NH₂, —N[(C₁-C₁₂)-alkyl]₂.

(C₃-C₁₂)-Cycloalkyl may in each case be unsubstituted or substituted by one or more identical or different radicals selected from (C₁-C₁₂)-alkyl, (C₁-C₁₂)-alkoxy, (C₃-C₁₂)-cycloalkyl, (C₃-C₁₂)-heterocycloalkyl, (C₆-C₂₀)-aryl, fluorine, chlorine, cyano, formyl, acyl and alkoxycarbonyl.

All ranges described herein include al values and subvalues between the upper and lower limits of such ranges.

In the context of the invention, the expression "—(C₁-C₁₂-alkyl" encompasses straight-chain and branched alkyl groups. Preferably, these groups are unsubstituted straight-chain or branched —(C₁-C₈)-alkyl groups and most preferably —(C₁-C₆)-alkyl groups. Examples of (C₁-C₁₂)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

Substituted —(C₁-C₁₂)-alkyl groups may have one or more substituents, depending on their chain length. The substituents are preferably each independently selected from —(C₃-C₁₂)-cycloalkyl, —(C₃-C₁₂)-heterocycloalkyl, —(C₆-C₂₀)-aryl, fluorine, chlorine, cyano, formyl, acyl or alkoxycarbonyl.

The expression "—(C₃-C₁₂)-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl.

Substituted —(C₃-C₁₂)-cycloalkyl groups may have one or more (e.g. 1, 2, 3, 4 or 5) further substituents, depending on their ring size. These substituents are preferably each independently selected from —(C₁-C₁₂)-alkyl, —(C₁-C₁₂)-alkoxy, —(C₃-C₁₂)-cycloalkyl, —(C₃-C₁₂)-heterocycloalkyl, —(C₆-C₂₀)-aryl, fluorine, chlorine, cyano, formyl, acyl or alkoxycarbonyl. Substituted —(C₃-C₁₂)-cycloalkyl groups preferably bear one or more (C₁-C₆)-alkyl groups. Substituted —(C₃-C₁₂)-heterocycloalkyl groups preferably bear one or more —(C₁-C₆)-alkyl groups.

In the context of the present invention, the expression "—(C₆-C₂₀)-aryl" encompasses mono- or polycyclic aromatic hydrocarbyl radicals. These have 6 to 20 ring atoms, more preferably 6 to 14 ring atoms, especially 6 to 10 ring atoms. Aryl is preferably —(C₆-C₁₀)-aryl and —(C₆-C₁₀)-aryl-(C₆-C₁₀)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —(C₆-C₂₀)-aryl groups may have one or more (e.g. 1, 2, 3, 4 or 5) substituents, depending on the ring size. These substituents are preferably each independently selected from —H, —(C₁-C₁₂)-alkyl, —O—(C₁-C₁₂)-alkyl, —O—(C₆-C₂₀)-aryl, —(C₆-C₂₀)-aryl, -halogen (such as Cl, F, Br, I), —COO—(C₁-C₁₂)-alkyl, —CONH—(C₁-C₁₂)alkyl, —(C₆-C₂₀)-aryl-CON[(C₁-C₁₂)-alkyl]₂, —CO—(C₁-C₁₂)-alkyl, —CO—(C₆-C₂₀)-aryl, —COOH, —OH, —SO₃H, —SO₃Na, —NO₂, —CN, —NH₂, —N[(C₁-C₁₂)-alkyl]₂.

Substituted —(C₆-C₂₀)-aryl groups are preferably substituted —(C₆-C₁₀)-aryl groups and —(C₆-C₁₀)-aryl-(C₆-C₁₀)-aryl groups, especially substituted phenyl or substituted naphthyl or substituted anthracenyl. Substituted —(C₆-C₂₀)-aryl groups preferably bear one or more, for example 1, 2, 3, 4 or 5, substituents selected from —(C₁-C₁₂)-alkyl groups, —(C₁-C₁₂)-alkoxy groups.

In one embodiment, R¹ is —(C₁-C₁₂)-alkyl.
In one embodiment, R¹ is —CH₂CH₃.

In one embodiment, at least one of the $R^1$, $R^2$, $R^3$ radicals is not the same as the two other radicals.

In one embodiment, $R^1$ is not the same as one of the $R^2$, $R^3$ radicals.

In one embodiment, $R^{41}$, $R^{42}$, $R^{43}$, $R^{44}$, $R^{45}$, $R^{51}$, $R^{52}$, $R^{53}$, $R^{54}$, $R^{55}$, $R^{61}$, $R^{62}$, $R^{63}$, $R^{64}$, $R^{65}$ are each independently selected from:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl.

In one embodiment, $R^{41}$, $R^{43}$, $R^{51}$, $R^{53}$, $R^{61}$, $R^{63}$ are each tert-butyl.

In one embodiment, $R^{45}$, $R^{55}$, $R^{65}$ are each —H.

In one embodiment, the mixture is solid at 25° C.

The term "solid" in this context is understood to mean the state of matter, which delimits the mixture, for example, from a liquid mixture.

As well as the mixture, a complex mixture including such a mixture is also claimed.

Complex mixture comprising:
an above-described mixture,
a metal atom selected from: Rh, Ru, Co, Ir.

In this regard, see R. Franke, D. Selent, A. Börner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff., p. 233 ff. and references cited therein, and also K. D. Wiese and D. Obst in Top. Organomet. Chem. 2006, 18, 1-13; Springer Verlag Berlin Heidelberg 2006 p. 6 ff. and references cited therein.

In the complex mixture, three different cases may exist:
1) The complex has ligands either of the I or II type, and the mixture is of complex molecules having only ligands of the I type with complex molecules having only ligands of the II type.
2) A complex in itself already has ligands of the I and II type.
3) Is a mixed form of 1) and 2).

As well as the mixtures/complex mixtures, also claimed is the use thereof as complex mixtures for catalysis of a hydroformylation reaction. In this case, the compounds in the mixture are the ligands in the complex. The ligands coordinate to the central metal atom. The ligand-metal complex thus obtained or the complex mixtures thus obtained then catalyze the hydroformylation reaction.

Use of an Above-Described Mixture in a Complex Mixture for Catalysis of a Hydroformylation Reaction.

In addition, also claimed is the hydroformylation reaction.

Process comprising the process steps of:
a) initially charging an olefin,
b) adding a mixture comprising a compound of the structure IIIa:

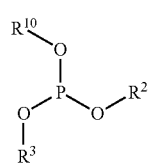

IIIa where
$R^{10}$ is selected from:
—$(C_1\text{-}C_{12})$-alkyl, —$(C_6\text{-}C_{20})$-aryl, —$(C_3\text{-}C_{12})$-cycloalkyl,
and $R^2$, $R^3$ are each independently selected from:
—$(C_1\text{-}C_{12})$-alkyl, —$(C_6\text{-}C_{20})$-aryl, —$(C_3\text{-}C_{12})$-cycloalkyl,
the $R^2$ and $R^3$ radicals may also be bridged to one another, and may have a —$(C_6\text{-}C_{20})$-aryl-$(C_6\text{-}C_{20})$-aryl unit,
where the alkyl, cycloalkyl and aryl groups mentioned may be substituted,
and a compound of the structure IIa:

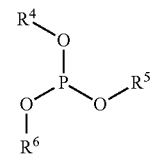

IIa where
$R^4$, $R^5$, $R^6$ are each independently selected from:
—$(C_1\text{-}C_{12})$-alkyl, —$(C_6\text{-}C_{20})$-aryl, —$(C_3\text{-}C_{12})$-cycloalkyl,
two $R^4$ and $R^5$ or $R^5$ and $R^6$ or $R^6$ and $R^4$ radicals may also be bridged to one another, and may have a —$(C_6\text{-}C_{20})$-aryl-$(C_6\text{-}C_{20})$-aryl unit,
where the alkyl, cycloalkyl and aryl groups mentioned may be substituted;
c) adding a compound comprising one of the following metals: Rh, Ru, Co, Ir,
c) feeding in $H_2$ and CO,
d) heating the reaction mixture, with conversion of the olefin to an aldehyde,
where the additions in process steps b) and c) can also be effected in one step through the addition of a corresponding complex mixture.

In this process, process steps a) to e) can be effected in any desired sequence.

Preference is given to a temperature of 80° C. to 160° C. and a pressure of 1 to 300 bar.

Particular preference is given to a temperature of 100° C. to 160° C. and a pressure of 15 to 250 bar.

In one variant of the process, $R^{10}$ is selected from: —$(C_1\text{-}C_{12})$-alkyl, —$(C_3\text{-}C_{12})$cycloalkyl.

In one variant of the process, $R^{10}$ is selected from: —$(C_1\text{-}C_{12})$-alkyl.

In one variant of the process, the mixture comprises a compound of the structure IIIb:

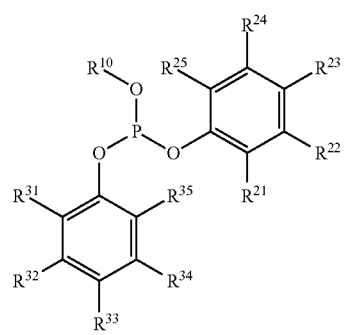

IIIb where
$R^{21}$, $R^{22}$, $R^{23}$, $R^{24}$, $R^{25}$, $R^{31}$, $R^{32}$, $R^{33}$, $R^{34}$, $R^{35}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen, —COO—($C_1$-$C_{12}$)-alkyl, —CO—($C_1$-$C_{12}$)-alkyl, —CO—($C_6$-$C_{20}$)-aryl, —COOH, —OH.

In one variant of the process, $R^{21}$, $R^{22}$, $R^{23}$, $R^{24}$, $R^{25}$, $R^{31}$, $R^{32}$, $R^{33}$, $R^{34}$, $R^{35}$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl.

In one variant of the process, $R^{21}$, $R^{23}$, $R^{31}$, $R^{33}$ are each tert-butyl.

In one variant of the process, $R^{25}$, $R^{35}$ are each —$CH_3$.

In one variant of the process, $R^{10}$ is —($C_1$-$C_{12}$)-alkyl.

In one variant of the process, $R^{10}$ is —$CH_2CH_3$.

In one variant of the process, $R^{10}$ is not the same as one of the $R^4$, $R^5$, $R^6$ radicals.

In one variant of the process, at least one of the $R^{10}$, $R^2$, $R^3$ radicals is not the same as the two other radicals.

In one variant of the process, $R^4$, $R^5$, $R^6$ are each independently —($C_6$-$C_{20}$)-aryl.

In one variant of the process, the mixture comprises a compound of the structure IIb

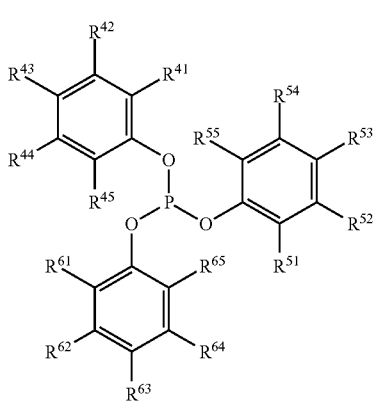

IIb where
$R^{41}$, $R^{42}$, $R^{43}$, $R^{44}$, $R^{45}$, $R^{51}$, $R^{52}$, $R^{53}$, $R^{54}$, $R^{55}$, $R^{61}$, $R^{62}$, $R^{63}$, $R^{64}$, $R^{65}$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen, —COO—($C_1$-$C_{12}$)-alkyl, —CO—($C_1$-$C_{12}$)-alkyl, —CO—($C_6$-$C_{20}$)-aryl, —COOH, —OH.

In one variant of the process, $R^{41}$, $R^{42}$, $R^{43}$, $R^{44}$, $R^{45}$, $R^{51}$, $R^{52}$, $R^{53}$, $R^{54}$, $R^{55}$, $R^{61}$, $R^{62}$, $R^{63}$, $R^{64}R^{65}$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl.

In one variant of the process, $R^{41}$, $R^{43}$, $R^{51}$, $R^{53}$, $R^{61}$, $R^{63}$ are each tert-butyl.

In one variant of the process, $R^{45}$, $R^{55}$, $R^{65}$ are each —H.

In a preferred embodiment, the metal is Rh.

The reactants for the hydroformylation in the process of the invention are olefins or mixtures of olefins, especially monoolefins having 2 to 24, preferably 3 to 16 and more preferably 3 to 12 carbon atoms, having terminal or internal C=C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures prepared by cooligomerization of olefins having different numbers of carbon atoms (preferably 2 to 4).

The process according to the invention using the mixtures/complex mixtures according to the invention can be used to hydroformylate α-olefins, terminally branched, internal and internally branched olefins. What is remarkable is the high yield of terminally hydroformylated olefin, even when only a small proportion of olefins having a terminal double bond was present in the reactant.

Having generally described this invention, a further understanding can be obtained by reference to certain specific examples which are provided herein for purposes of illustration only, and are not intended to be limiting unless otherwise specified.

EXAMPLES

General Operating Procedures

All the preparations which follow were carried out under protective gas using standard Schlenk techniques. The solvents were dried over suitable desiccants before use (Purification of Laboratory Chemicals, W. L. F. Armarego, Christina Chai, Butterworth Heinemann (Elsevier), 6th edition, Oxford 2009).

All preparative operations were effected in baked-out vessels. The products were characterized by means of NMR spectroscopy. Chemical shifts (δ) are reported in ppm. The $^{31}P$ NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

Nuclear resonance spectra were recorded by means of a Broker Avance 300 or Bruker Avance 400; gas chromatography analysis was effected using an Agilent GC 7890A.

Preparation of
bis(2,4-di-tert-butyl-6-methylphenyl)ethyl phosphite

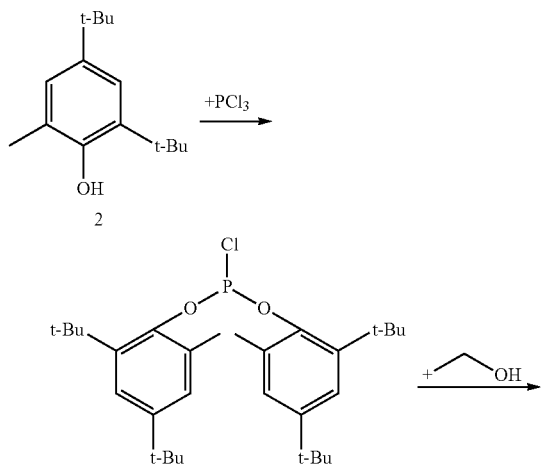

-continued

[Structure: Ligand with OCH₂CH₃ on phosphorus, bis(2,4-di-tert-butyl-6-methyl)phenyl phosphite]

A 250 ml Schlenk flask with magnetic stirrer, attachment, dropping funnel and reflux condenser was initially charged with 22.5 g (0.1 mol) of 2,4-di-tert-butyl-6-methylphenol (4,6-di-tert-butyl-ortho-cresol), and heated to 55° C. in order to melt the phenol. 0.13 ml (0.0015 mol) of dried degassed dimethylformamide was added to the melt. Subsequently, 5.7 ml (0.065 mol) of phosphorus trichloride were added dropwise within 2 hours. After the addition had ended, the reaction mixture was heated to 140° C. within 3 hours and stirred at this temperature for 1 hour. Then the mixture was stirred at 130° C. under reduced pressure for 1 hour. Thereafter, the clear yellow-orange melt obtained (=bis(2,4-di-tert-butyl-6-methyl)phosphochloridite) was cooled down to 80° C. overnight and diluted with 75 ml of degassed petroleum (80-110° C.). After the solution had been cooled down to −5° C., 9.1 ml (0.0665 mol) of degassed triethylamine were added within 15 minutes. Subsequently, within 2 hours, 4.4 ml (0.075 mol) of dried and degassed ethanol were added dropwise, in the course of which the temperature did not rise above 5° C. This mixture was warmed gradually to room temperature overnight while stirring.

The next morning, the precipitated triethylamine hydrochloride was filtered off and the filtrate was concentrated under reduced pressure. This gave a white residue which was recrystallized in 60 ml of degassed ethanol. The product was thus obtained in a yield of 73.9% (19.03 g) as a white solid in 98% purity by LC-MS.

Procedure for the Catalysis Experiments
Experiment Description—General

In a 100 ml autoclave from Parr Instruments, n-octenes were hydroformylated at 120° C. and synthesis gas pressure 50 bar (CO/H$_2$=1:1 (% by vol.)). As precursor, 0.123 g of Rh(acac)(CO)$_2$ was initially charged for a catalyst concentration of 100 ppm of Rh based on the overall reaction mixture. The solvent used was 40 to 46 g of toluene in each case. Ligand 1 or ligand 2 or the ligand mixture consisting of ligands 1 and 2 was used in different molar excesses relative to rhodium. In addition, as GC standard, about 0.5 g of tetraisopropylbenzene (TIPB) was added. About 6 g of reactant were metered in after the reaction temperature envisaged had been attained.

During the reaction, the pressure was kept constant via synthesis gas regulation with a mass flow meter. The stirrer speed was 1200 min$^{-1}$. Samples were taken from the reaction mixture after 12 hours. The results of the experiments are summarized in Table 1.

(acac=acetylacetonate)
Ligands Used in the Catalysis Experiments:

[Structure 1: Ligand with OCH₂CH₃ on phosphorus]

[Structure 2: TDTBPP ligand]

The preparation of ligand 1 is described in the above experimental section. Ligand 2 (TDTBPP or Alkanox 240) is commercially available.

Table 1 gives the results for the hydroformylation of di-n-butene. Di-n-butene is a mixture of isomers of n-octenes (about 16%), 3-methylheptenes (about 65%) and 3,4-dimethylhexenes (about 19%).

(Yield=total aldehyde and alcohol yield; S=n/iso selectivity of the octenes present in the mixture for the linear product)

TABLE 1

| Entry | Ligand A | Ligand B | Ligand A in [mmol] | Ligand B in [mmol] | Y in % | S in % |
|---|---|---|---|---|---|---|
| 1 | — | 2 | — | 20** | 96.9 | 21.8 |
| 2* | 1 | 2 | 0.62 | 0.32 | 95.9 | 36.4 |
| 3* | 1 | 2 | 0.47 | 0.47 | 95.7 | 24.6 |
| 4* | 1 | 2 | 0.31 | 0.62 | 95.5 | 23.4 |

Reaction conditions: synthesis gas pressure 50 bar, T = 140° C., substrate: di-n-butene, P:Rh = 20:1; 100 ppm [Rh], 12 hours
*inventive mixture or complex mixtures
**ratio of ligand to Rh 20:1

Table 1 contains experiments for hydroformylation of di-n-butene with various mixtures/complex mixtures. Entry 1 contains a comparative experiment which was conducted with ligand 2 only. A good yield was achieved here, but the selectivity leaves something to be desired.

Through the use of the inventive mixtures/complex mixtures, it was possible to increase the selectivity in all cases. Selectivity for the desired linear aldehydes is noticeably greater here than in the case of the commercially available ligand 2. No significant deterioration is apparent in the yields.

Through the use of the inventive mixtures/complex mixtures, it is possible to selectively control and increase the proportion of terminally hydroformylated product.

The process according to the invention using the mixtures/complex mixtures according to the invention can be used to hydroformylate α-olefins, terminally branched, internal and internally branched olefins. What is remarkable is the high yield of terminally hydroformylated olefin, even when only a small proportion of olefins having a terminal double bond was present in the reactant.

It was thus possible to show, with the aid of the above examples, that the stated problems have been solved through the use of the inventive mixtures/complex mixtures.

German patent application no. DE102014209535.2 filed May 20, 2014, and German patent application no. DE102015202722.8 filed Feb. 16, 2015, are incorporated herein by reference.

Numerous modifications and variations on the present invention are possible in light of the above teachings. It is

The invention claimed is:

1. A mixture, which comprises a mixture of compounds 1 and 2:

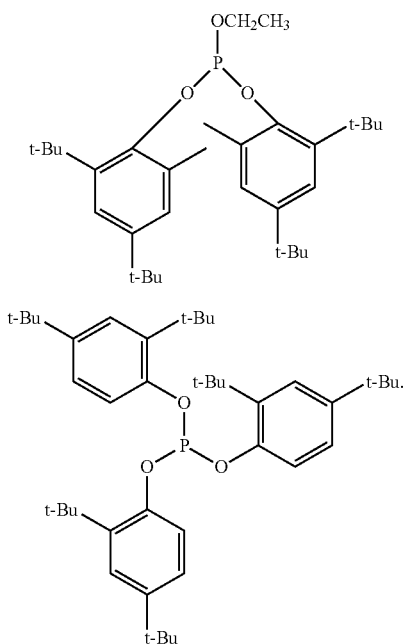

2. A complex mixture, comprising:
are according to claim 1, and
a metal atom selected from the group consisting of Rh, Ru, Co, and Ir.

3. The complex mixture according to claim 2, wherein said metal atom is Rh.

4. A process for hydroformylation of an olefin, comprising:
a) initially charging an olefin,
b) adding a mixture according to claim 1
c) adding a compound comprising one of the following metals: Rh, Ru, Co, or Ir, to obtain a reaction mixture,
c) feeding $H_2$ and CO into the reaction mixture,
d) heating the reaction mixture, to convert the olefin to an aldehyde,
wherein the additions in process steps b) and c) can also be effected in one step through the addition of a corresponding complex mixture.

5. The process according to claim 4, wherein the olefin is a mono-olefin having 2 to 24 carbon atoms, and having a terminal or an internal C=C double bond.

6. The process according to claim 4, wherein the olefin is an α-olefin, terminally branched, internal and internally branched olefin.

7. The process according to claim 4, wherein a terminally hydroformylated olefin is obtained.

* * * * *